United States Patent
Davis et al.

(10) Patent No.: US 10,463,444 B2
(45) Date of Patent: Nov. 5, 2019

(54) LIGHT CARRIER AND SYSTEM FOR MOUNTING SAME TO A SURGICAL INSTRUMENT

(71) Applicants: James M. Davis, Naples, FL (US); Kim A. Marsh, Naples, FL (US)

(72) Inventors: James M. Davis, Naples, FL (US); Kim A. Marsh, Naples, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 432 days.

(21) Appl. No.: 15/172,764

(22) Filed: Jun. 3, 2016

(65) Prior Publication Data
US 2016/0361133 A1     Dec. 15, 2016

Related U.S. Application Data

(60) Provisional application No. 62/170,313, filed on Jun. 3, 2015.

(51) Int. Cl.
| | |
|---|---|
| *A61B 90/35* | (2016.01) |
| *A61B 17/3211* | (2006.01) |
| *A61B 17/02* | (2006.01) |
| *A61B 90/30* | (2016.01) |

(52) U.S. Cl.
CPC ............ *A61B 90/35* (2016.02); *A61B 17/02* (2013.01); *A61B 17/3211* (2013.01); *A61B 17/0206* (2013.01); *A61B 2090/306* (2016.02)

(58) Field of Classification Search
CPC ......... A61B 90/35; A61B 90/30; A61B 17/02; A61B 17/0206; A61B 17/3211; A61B 17/3213; A61B 17/3215; F21V 21/0885; F21L 4/04

See application file for complete search history.

(56) References Cited

U.S. PATENT DOCUMENTS

| | | | | |
|---|---|---|---|---|
| 2,566,886 | A * | 9/1951 | Hartman | F16B 2/246 24/458 |
| 3,300,168 | A * | 1/1967 | Gaudino | B60R 7/08 24/326 |
| 3,983,602 | A * | 10/1976 | Barry | A42B 3/04 24/11 R |
| 6,430,782 | B1 * | 8/2002 | Torres | A24F 15/18 206/87 |
| 6,932,186 | B2 * | 8/2005 | Costa | A61B 7/02 181/131 |
| 7,021,790 | B2 * | 4/2006 | Parsons | A44B 15/005 362/116 |
| 2010/0030033 | A1 * | 2/2010 | Farley | A61B 1/07 600/249 |

* cited by examiner

*Primary Examiner* — Christian A Sevilla
(74) *Attorney, Agent, or Firm* — William E. Noonan (57) ABSTRACT

A releasable light carrier mounting frame includes an upper portion having a receptacle for receiving a light carrier. One or more clips are attached to the upper portion and engaged with an underlying surgical instrument to secure the light carrier to the surgical instrument.

9 Claims, 8 Drawing Sheets

LIGHT CARRIER AND SYSTEM FOR MOUNTING SAME TO A SURGICAL INSTRUMENT

RELATED APPLICATION

This application claims the benefit of U.S. Provisional Application Ser. No. 62/170,313 filed Jun. 3, 2015.

FIELD OF THE INVENTION

This invention relates to light transmitting surgical instruments and more particularly, to a light carrier and a mounting system used to releasably secure a light carrier to an underlying surgical instrument so that light may be conducted through and transmitted from the instrument to better illuminate a surgical or medical procedure.

BACKGROUND OF THE INVENTION

Various types of surgical and medical instruments have been modified to conduct and project light in order to illuminate and thereby facilitate medical and surgical procedures. In some of these instruments, the surgical instrument itself is composed of a light conducting and projecting material that is attached to a fiberoptic light source. See, for example, U.S. Pat. Nos. 5,931,670, 6,059,723, 6,304,712 and 6,176,824. This technology has been utilized in dental suction devices, tongue depressors, surgical retractor blades, forceps, vaginal specula and laryngoscopes, among other instruments. In other instruments, a light guide or carrier attached to the fiberoptic light source is mounted in a channel and/or secured by tabs formed integrally in the surgical device. This is the conventional practice disclosed, for example, in U.S. Pat. Nos. 8,088,066 and 8,920,316.

Forming an integral channel and/or tabs in a retractor or other surgical instrument for holding a light carrier must be performed when the instrument is manufactured. This adds a considerable amount of complexity and expense to design and fabrication of the surgical instrument. The overwhelming majority of existing surgical devices simply do not have the built-in capacity to hold a light carrier so that it may be used effectively during a surgical or medical procedure in order to better illuminate the area of the patient on which the procedure is being performed. Currently, there is no procedure or device available for retrofitting standard surgical tools to accommodate a surgical illuminating light carrier or guide. A need likewise exists for an improved surgical light carrier that not only is conveniently adapted for use with standard retractors and other surgical tools, but that also achieves reduced light transmission losses and therefore better illumination of surgical procedures than is exhibited by conventional tools

SUMMARY OF THE INVENTION

It is therefore an object of the present invention to provide an improved illuminated surgical instrument featuring a releasable mounting system that securely attaches a light carrier to a surgical instrument so that improved illumination of a surgical site is achieved.

It is a further object of this invention to provide a releasable light carrier mounting system that eliminates the need to specially configure and fabricate a surgical instrument to include a custom slot, channel or tabs for attaching a light carrier to the instrument and which therefore reduces the expense and complexity of manufacturing such surgical instruments.

It is a further object of this invention to provide a releasable light carrier mounting system that may be used to quickly, conveniently and effectively secure a fiberoptically compatible light carrier to virtually any standard surgical instrument without having to structurally modify the instrument.

It is a further object of this invention to provide a releasable light carrier mounting system that is attached quickly and easily to a surgical instrument and which does not interfere with use of the instrument during a surgical or medical procedure.

It is a further object of this invention to provide a releasable light carrier mounting system that attaches onto a surgical or medical instrument simply and quickly so that valuable time is saved in preparing for surgery.

It is a further object of this invention to provide a releasable light carrier mounting system employing lightweight and inexpensive materials and a simple, yet efficient design which allows the frame to be either disposable or reusable as preferred and/or required.

It is a further object of this invention to provide a releasable light carrier mounting system that is readily adjusted to accommodate and securely hold light carriers having various configurations and dimensions.

It is a further object of this invention to provide a releasable light carrier mounting system that does not impede the movement of a surgeon or other medical professional or interfere with the use of surgical equipment during a surgical procedure.

It is a further object of this invention to provide an improved light carrier employing a configuration that transforms transmitted light from a relatively narrowly focused beam to a more broadly radiated light pattern so that improved illumination of surgical and medical procedures is achieved.

This invention results from a realization that a light transmitting carrier or guide may be quickly, conveniently and yet effectively secured to a surgical retractor blade or virtually any other type of surgical instrument through the use of a thin, lightweight, adjustable and nonobtrusive mounting system that may be manipulated to releasably attach the light carrier to the underlying surgical instrument. Such a device eliminates the need to form integral slots, channels and/or tabs in the surgical instrument and allows virtually any such instrument to be quickly and conveniently retrofit to accommodate a light carrier for effectively illuminating a medical or surgical procedure.

This invention features a releasable light carrier mounting system for a surgical instrument. The system includes an upper frame portion for holding the light carrier to be mounted on the surgical instrument. At least one retaining clip is attached to the upper frame portion for depending downwardly therefrom and wrapping about or otherwise engaging the surgical instrument to releasably secure the light carrier to the surgical instrument. The upper frame portion is disposed peripherally about and exposes a light projecting portion of the light carrier. The light carrier is communicably connected to a fiberoptic light source such that light from the light source is transmitted through the light carrier and projected from the exposed light projecting portion.

In a preferred embodiment, the upper frame portion includes a receptacle for receiving the light carrier. The upper frame portion may have a rectangular shape that surrounds or encloses a rectangular interior opening through which the light carrier is exposed. The receptacle may be defined by slots formed respectively in a pair of longitudinal sides of the rectangular upper frame portion and a transverse end of the upper frame portion interconnecting the longitudinal sides. A plurality of deformably bendable retaining clips may be attached to and extend outwardly from the longitudinal pieces of the upper frame portion. Each retaining clip may include a flexible arm with a self-sustaining shape that may be manipulated to wrap about the surgical instrument and secure the frame in place about the surgical instrument with the light carrier covered by the upper frame portion and accommodated within the receptacle of the upper frame portion. A pair of retaining clips may be formed along each of the opposing longitudinal sides of the rectangular upper frame portion in an offset arrangement. Each clip may include a rounded tab that is unitarily carried at a distal end of the clip and depends therefrom. Typically, each retaining clip and unitary tab have a flexible, self-sustaining shape that may be readily manipulated to conform to the particular dimensions and shapes of the underlying surgical instrument and light carrier supported thereon. For example, in one version, each clip may be bent a first time to engage a respective edge of the light carrier, a second time to engage an upper surface of the surgical instrument, a third time to engage a side edge of the surgical instrument and a fourth time to engage a bottom surface of the instrument. Accordingly, the bendable clips may be deformably manipulated to effectively wrap around the surgical instrument and thereby securely hold the light carrier against the surgical instrument. This configuration is especially effective where the surgical instrument comprises a retractor blade or other type of blade-like and bendable surgical instrument. Nonetheless, it should be understood that the mounting system may be used with instruments having a wide variety of alternative shapes and sizes.

In an alternative version of the invention, the mounting frame may include an upper receptacle for receiving a light carrier and a resilient retaining clip that is attached to and depends from the upper receptacle for engaging and releasably attaching to a surgical tool or other piece of medical equipment. The retaining clip may include a wall that depends from the upper receptacle and a curved backing element attached to a lower end of the depending wall and spaced apart from a base of the receptacle for defining a slot that receives the surgical instrument. The curved backing element bears resiliently against the surgical instrument such that the surgical instrument is retained between the curved backing element and the base of the receptacle. This secures the mounting frame to the surgical instrument.

In the above described alternative version, the upper receptacle may include a lip formed along one side of the receptacle for engaging a corresponding groove formed in the light carrier. The opposite side of the receptacle may be angled inwardly. The lip and the inwardly angled side help to hold the light carrier in place securely within the receptacle.

In still another embodiment, the upper frame portion may be formed unitarily or in a single piece with the light carrier and may be disposed peripherally about and connected unitarily to a supported light projecting portion of the light carrier. In such versions, one or more retaining clips may be attached unitarily to the upper frame portion. Such retaining clips may include a resilient construction that allows the retaining clips to interengage and releasably secure to a retractor blade or other type of surgical instrument. In this manner, the light carrier and, more particularly, the supported light projecting portion of the light carrier, are releasably mounted to the retractor or other surgical instrument to project light from the instrument during a surgical or other medical procedure.

This invention also features a one-piece light carrier that is releasably attachable to a surgical instrument. The light carrier includes an inlet section composed of a light conductive material for communicably interconnecting to a light source (e.g. a fiberoptic illuminator and appropriate fiberoptic cable). An intermediate rod section having a circular cross sectional shape is likewise composed of the light-conducting material and is communicably and unitarily interconnected to the inlet section for transmitting light from the inlet section therethrough. The intermediate rod section includes a longitudinally curved neck. An elongate distal blade section having generally flat upper and lower surfaces is likewise composed of the light-conducting material. A transition section, which is also composed of the light-conducting material, communicably and unitarily interconnects the rod section and the blade section. The transition section features a narrowing taper from the rod section to the blade section such that the blade section has a thickness that is less than the diameter of the rod section. By the same token, the transition section includes a narrowing taper extending from the opposing longitudinal edges of the blade section to the rod section such that the blade section has a transverse width that is greater than the diameter of the rod section. As a result, light transmitted through the rod section in essentially the form of a beam, is broadened by the transition section and transmitted through the blade section in a broader, dispersed pattern. As a result, the light transmitted through the blade section is radiated from at least one surface of the blade section in order to effectively illuminate a surgical procedure.

Preferably, one or more clips may be unitarily connected to and carried by the blade section for releasably securing the light carrier to a surgical instrument. Such clips are selectively expanded to engage a retractor or other instrument. A thickened overlay, overmold or other opaque substance may be carried by the rod section to reduce light dissipation and loss through the rod section.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

Figure 1:
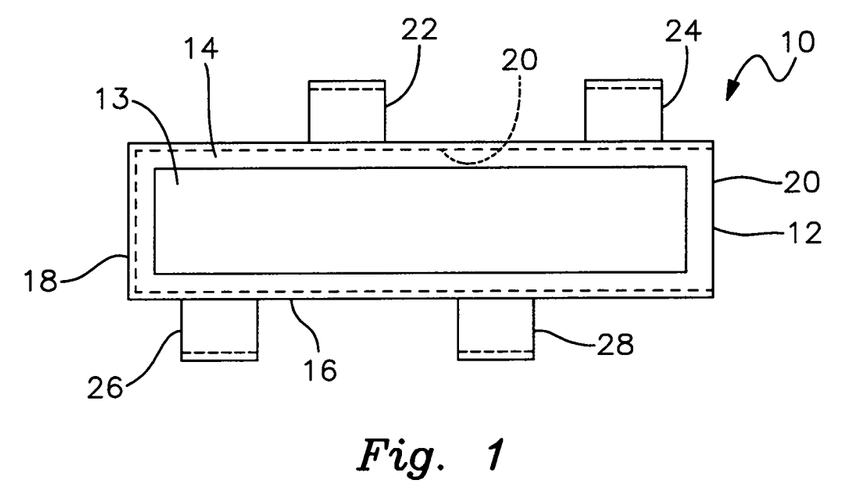
FIG. 1 is a plan view of preferred light carrier mounting frame for surgical instruments in accordance with this invention.
Figure 2:
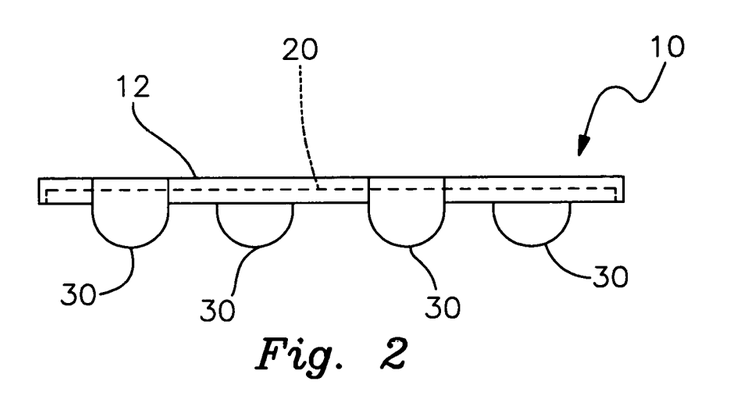
FIG. 2 is an elevational side view of the preferred mounting frame.
Figure 3:
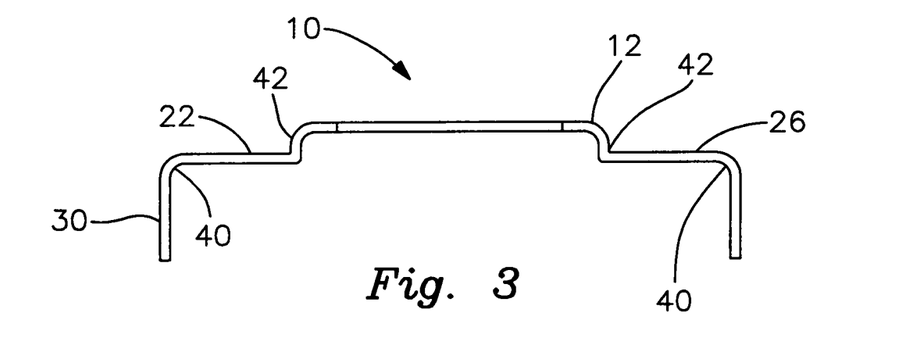
FIG. 3 is an elevational end view of the preferred mounting frame.

There is shown in FIGS. 1-3 a light carrier mounting system comprising a frame 10 for attaching a light conductive and transmissive carrier element (not shown in FIGS. 1-3, but see carriers C-C3 in FIGS. 4-7 respectively) to an underlying surgical instrument in accordance with this invention. It should be understood that the mounting frame may be used with virtually any light guide, light carrier or other type of component that is attachable to a fiberoptic light source and which conducts light therethrough and projects the light in order to better illuminate a medical or surgical procedure. The variety and composition of the light carrier itself are not limitations of this invention. Moreover, the mounting frame may be employed with virtually any type of surgical instrument including, but not limited to surgical retractors, clamps, forceps, etc. In addition, the mounting frame may be employed effectively in any surgical or medical procedure where improved illumination is needed and/or desired.

Mounting frame 10 includes a rectangular upper frame portion 12 having a pair of longitudinal side pieces 14, 16 interconnected by transverse ends 18 and 20 that extend between the respective ends of pieces 14 and 16. A light carrier receptacle 20 is effectively defined by longitudinal slots formed in the respective bottoms of side pieces 14, 16 and one of the transverse end pieces (i.e. end piece 18 interconnecting pieces 14 and 16). This defines a slotted receptacle for receiving the light carrier in a manner described more fully below. An opening 13 is formed centrally through upper frame portion 12. The opening serves to project transmitted light therethrough in a manner that will be described more fully below.

A retaining clip portion includes a plurality of deformably bendable fastening clips 22, 24, 26 and 28 are secured unitarily to the side pieces of upper frame portion 12 such that clips 22 and 24 attached to piece 14 are staggered or offset relative to clips 26 and 28 fastened to piece 16. The fastening clips are unitarily joined to the upper frame portion such that the entire mounting frame 10 is composed of a relatively thin, flexible and lightweight, yet strong and durable metal such as bendable aluminum or stainless steel. Each of clips 22, 24, 26 and 28 carries an integrally attached tab 30 that depends perpendicularly downwardly from the outer or distal end of the clip.

Mounting frame 10 may have various alternative sizes, shapes and thicknesses and compositions. The specific configuration and dimensions should not be deemed a limitation of this invention. The frame may be made sufficiently small or sufficiently large to fit on virtually any type of surgical or medical instrument in order to securely attach a light carrier of virtually any configuration to the instrument. Moreover, the central opening 13 may be configured and sized in accordance with the light carrier that is being mounted in a particular application. The opening should be sufficiently large to transmit a significant portion of the light projected from the light carrier therethrough.

Mounting frame 10 should be composed of a bendable material having a self-sustainable shape, particularly at interior corners 40 and exterior corners 42, The metallic material composing the support frame provides the frame with a self-sustaining shape so that clips 22-26 and integral tabs 30 may be bent into and maintained in a selected shape that allows the clips and tabs to effectively grip the mounting frame and secure that frame and an underlying light carrier to a surgical instrument. The flex exhibited by upper frame portion 12 allows the frame to better adapt and conform to the shape of a particular light carrier and/or surgical instrument.

Figure 4:
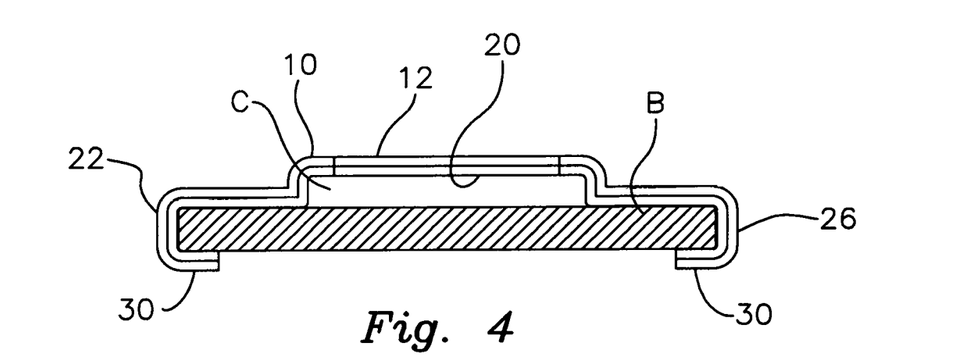
FIGS. 4 and 5 are cross sectional views of the mounting frame being configured and used to hold light carriers onto 23 mm and 14 mm surgical retractor blades respectively.

A light carrier C, FIG. 4, is mounted to the upper surface of a surgical blade B or other surgical instrument by manipulating support frame 10 and attachably engaging the support frame with the underlying blade B. First, light carrier C is inserted into peripheral receptacle slot 20 formed in segments 14, 16 and 18 of upper frame portion 12. Clips 22, 24, 26 and 28 are then bent and wrapped about the side edges of blade B such that respective distal tabs 30 of the clips interengage the bottom surface of surgical blade B. Only clips 22 and 26 and their dependent tabs 30 are shown in FIG. 4. However, it should be understood that clips 24 and 28 and the tabs dependent therefrom are manipulated to wrap about and interengage blade B in an analogous fashion. This securely mounts light carrier C to the underlying surgical instrument B.

Figure 5:
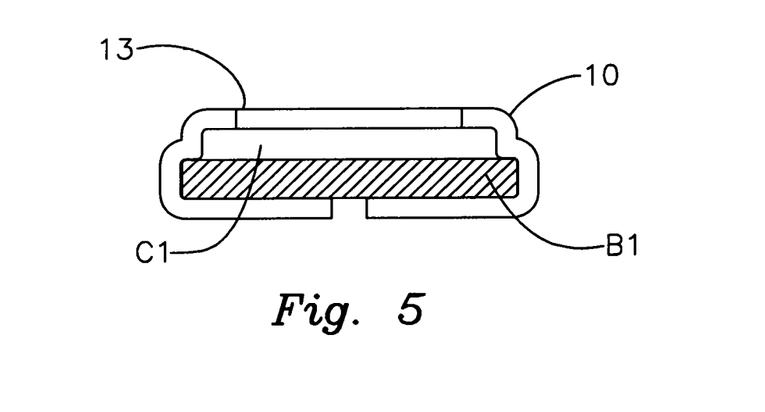

A light carrier mounted onto the top surface of a 23 mm blade is shown in FIG. 4. In FIG. 5 bendable light frame 10 is similarly wrapped about and interengaged with an underlying surgical instrument B1 comprising a 14 mm blade. As a result, central opening 13 is aligned with the underlying carrier C, C1 held in place by support frame 10. In either case, light conducted through and projected from the light carrier C, C1 is transmitted through the central opening 13 and onto the patient's bodily part undergoing a surgical or medical procedure.

Figure 6:
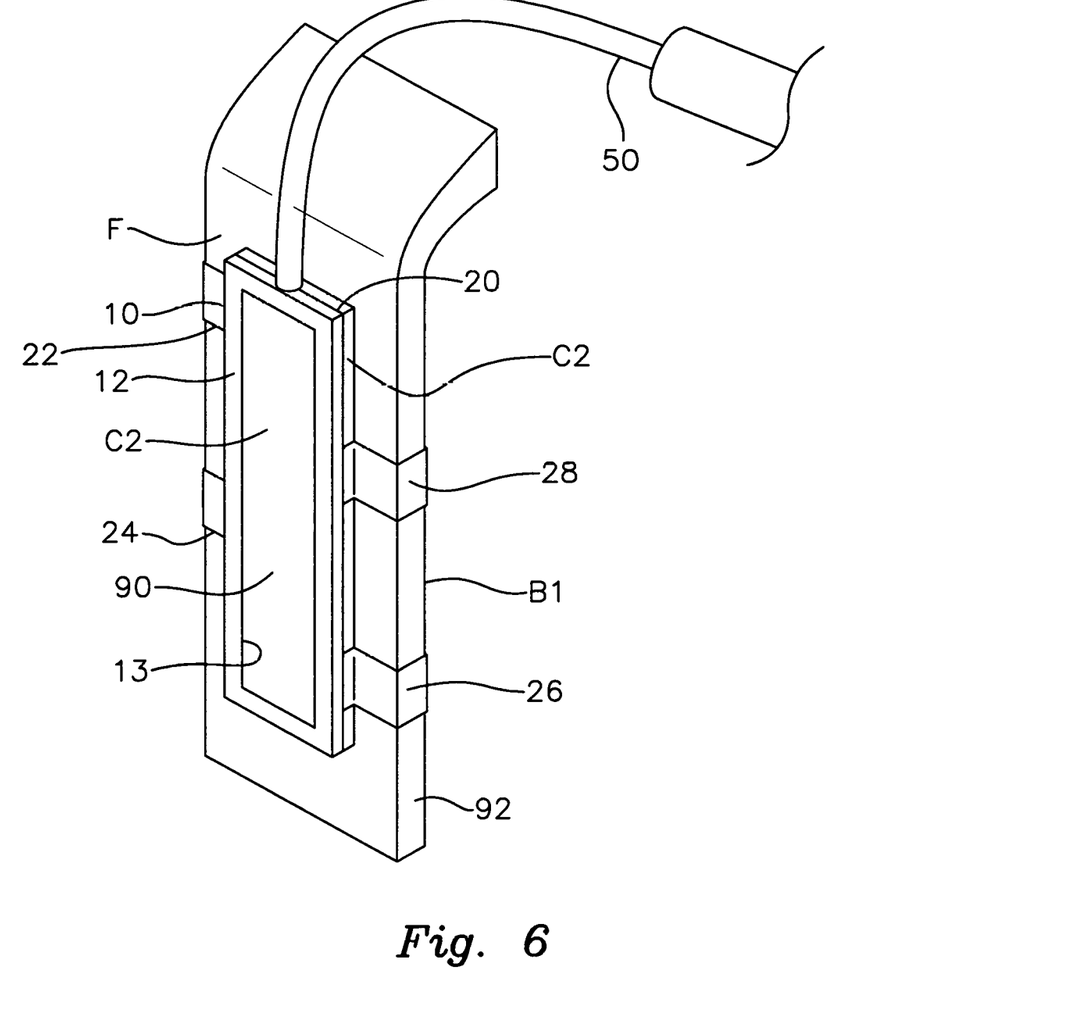
FIG. 6 is a perspective view depicting the mounting frame being used to hold a light carrier onto a surgical retractor blade.

There is shown in FIG. 6 a perspective view of a light carrier C2, which is releasably mounted to an underlying surgical instrument B1 by mounting frame 10. Once again, light carrier C2 is inserted into a slotted receptacle (not shown in FIG. 6 but see FIGS. 1-5) formed in the bottom of rectangular upper frame portion 12. Light carrier C2 is aligned within the slotted receptacle of the frame such that the broad surface 90 of light carrier C2 is aligned or registered with the central opening 13 in the mounting frame. Bendable clips 22, 24, 26 and 28 are manipulated such that they wrap about the front surface F and the side surfaces 92 (only one of which is shown in FIG. 6) of blade B1. The distal tips or tabs 30 carried by the clips interengage the obscured back or bottom surface of blade B1 in the manner previously described. As a result, light carrier C2 is securely mounted to the front surface F of surgical instrument B1. A fiberoptic cable 50 is operably connected to light carrier C2. The surgical instrument may then be used in a conventional manner during a medical or surgical procedure and the fiberoptic light source delivers light to light carrier C2, which light is projected outwardly from carrier C2 through central opening 13 of support frame 10. This provides improved illumination of the surgery site.

Figure 7:
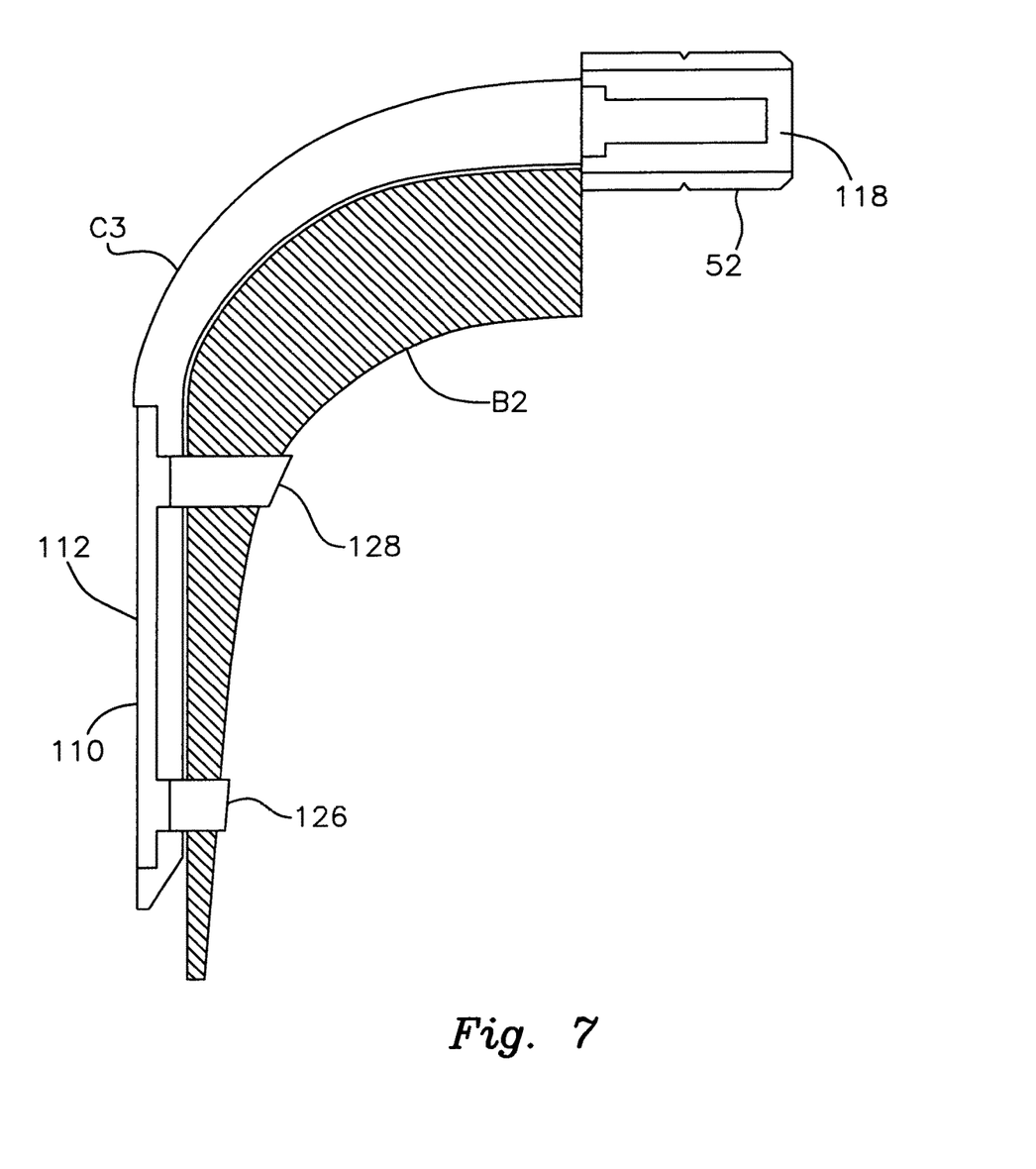
FIG. 7 is a side elevational, cross sectional view depicting the mounting frame operably interengaged with a surgical instrument and releasably attaching a light carrier mounted to the surgical instrument.

FIG. 7 illustrates an alternative retractor blade or other surgical instrument B2 on which a curved light carrier C3 is removably mounted. The light carrier is attached at its input end to a fiberoptic cable connector 52. The connector is, in turn, communicably connected to a fiberoptic light source through a fiberoptic cable (now shown).

Light carrier C3 is attached to underlying instrument B2 by means of a mounting system featuring a frame 110. The mounting frame is constructed in a manner analogous to that previously described and includes a unitary construction. The frame is composed of a lightweight, yet durable metal such as stainless steel or aluminum, which includes a bendable, self-sustaining shape. An upper frame portion 112 features a rectangular shape similar to that previously described. A central opening (not shown) is again formed through the upper frame portion. The upper frame portion again also includes a slotted bottom that slidably receives the light carrier C3. In this version, the light carrier mounting frame is shown engaged with a curved light carrier and an underlying surgical instrument. The light carrier may feature various compositions and may be flexible, semi-rigid or rigid. The underlying surgical instrument may also be flexible or rigid. In certain versions, the upper frame portion 112 may be curved or flexible to generally conform to the curvature and shape of light carrier C3. Upper frame portion 112 may extend for either longer or shorter distances along the length of light carrier C3 than shown in FIG. 6.

A pair of bendable dips 126 and 128, which are constructed analogously to the clips previously described, are attached to and extend outwardly from one longitudinal piece of upper frame portion 112. A similar pair of bendable clips are likewise attached to the upper mounting frame and extend from the opposite longitudinal side segment or piece of the upper frame portion in a manner similar to that previously described. After the mounting frame 110 is interengaged with light carrier C3 (by inserting the light carrier into the slotted receptacle formed in the bottom of the upper frame portion) the four clips are manipulated and wrapped around the sides and across the underneath surface of surgical instrument B2. Once again, distal tabs may be carried by the clips for engaging the bottom or underlying surface of instrument B2.

When mounting frame 110 is securely interengaged with both light carrier C3 and instrument B2, the light carrier is thereby securely fastened to the surgical instrument. The instrument may then be used in a standard manner with the light carrier illuminated to project light effectively onto a surgical area or other site of a medical procedure. The clips and slotted interengagement between the upper frame portion and the light carrier hold the light carrier securely in place so that it does not become accidentally detached or dislodged from the surgical instrument during surgery.

Figure 8:
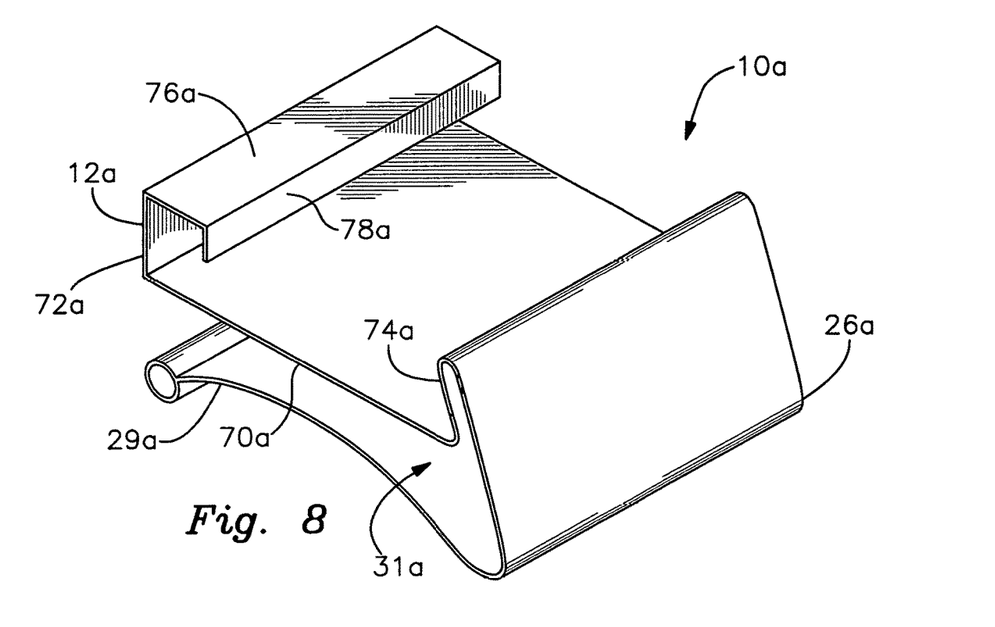
FIG. 8 is a perspective view of an alternative light carrier holder including a disposable spring clip.
Figure 9:
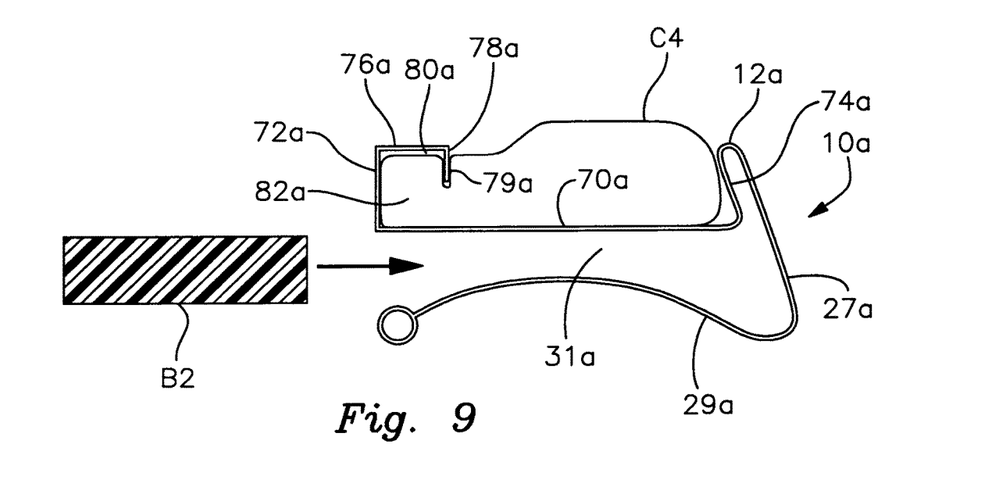
FIG. 9 is an end cross sectional view of the clip of FIG. 8 with a light carrier held therein and adjacent a surgical retractor to which the clip is attached.

There is shown in FIGS. 8 and 9 an alternative light carrier mounting system comprising a mounting frame 10a according to this invention. Mounting frame 10a comprises a unitary or one-piece spring clip featuring an upper frame portion, which is defined by a receptacle 12a, and a spring biased instrument retaining bracket or clip portion 26a unitarily attached to receptacle 12a. Mounting frame 10a is composed of a thin but durable metallic material that has some degree of resilience so that a light carrier and a surgical instrument may be conveniently interengaged with and gripped by the clip portion as is described below.

Upper receptacle portion 12a includes a base 70a, a first side wall 72a and an opposite second side wall 74a, which is resiliently biased toward and inclined inwardly relative to base 70a. An elongate strip 76a is attached to and extends perpendicularly from an upper end of side wall 72a. A retaining lip 78a depends from the inner end of strip 76a. As a result, upper receptacle portion 12a defines an interior channel 31a that accommodates a light carrier C4.

Figure 10:
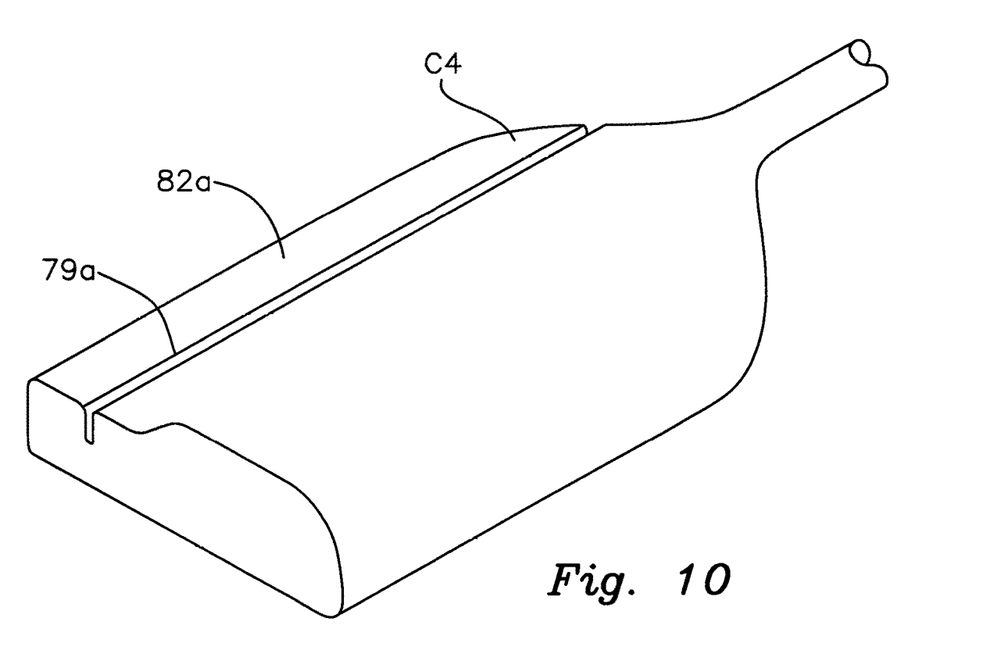
FIG. 10 is a perspective view of a light carrier used with the version of FIGS. 8 and 9.

Light carrier C4 is configured so that it is held snugly and securely within receptacle 12a of clip mounting frame 10a. In particular, one side of light carrier C4 is engaged by the inwardly angled side wall 74a of the channel portion. The bottom of the light carrier engages base 70a. Side 82a of the light carrier fits within a slot 80a defined by wall 72a, strap 76a and lip 78a. The light carrier includes a groove 79a that is engaged by complementary lip 78 such that the light carrier is held snugly within the upper receptacle of the mounting frame.

Spring biased retaining clip portion 26a includes a depending side wall 27a and a curved backing strip 29a that is attached to the lower end of depending wall 27a and spaced below base 70a. This forms a passageway 31a, which receives a retractor blade B2 or other surgical instrument. The curved backing 29a provides a spring tension that secures mounting frame 10a onto blade B2.

In use, light carrier C4 is inserted into upper receptacle portion 12a with the elongate groove 79a of light carrier C4 aligned with and receiving depending lip 78a of mounting frame 10a. One side 82a of carrier C4 is thereby snugly received by slot 80a of receptacle portion 12a, whereas the opposite side of the light carrier is snugly engaged by inwardly inclined and resiliently biased side wall 74a. Retractor B2 or some other surgical instrument is inserted either transversely (as shown in FIG. 9) or longitudinally into passageway 31a of the mounting frame. The retainer backing element 29a is spread apart from base 70a of upper receptacle 12a to allow the blade to be inserted into the passageway. When the backing element 29a is released, the spring tension of the retaining bracket causes the curved backing element 29a to bear against the bottom of the blade. As a result, mounting frame 10a and supported light carrier C4 are held securely in place on the blade.

The alternative version shown in FIGS. 8 and 9 operates analogously to and achieves benefits similar to those of the previously described version. The light carrier is thereby supported securely upon the underlying surgical instrument. Auxiliary lighting does not have to be hung onto nearby objects and areas which could impede movement of medical personnel during a surgical procedure or otherwise interfere with the usage of surgical instruments during such a procedure.

The light carrier mounting frame of the present invention provide for significant advantages over conventional means for attaching a light guide or light carrier to a surgical instrument. In particular, the mounting frame allows virtually all types of light carriers to be quickly, conveniently and securely attached to almost any type of surgical instrument. It is no longer necessary to specially construct or manufacture the surgical instrument with a special receiving slot or tabs for accommodating and holding the light carrier. This saves considerable manufacturing and equipment expense.

The mounting frame employs light weight and inexpensive material as well as a simple and cost efficient design. These features allow the mounting frame to be either disposable or reusable according to the needs and convenience of the medical facility using the frame.

The easily bendable and convenient self-sustaining shape employed by certain versions of the mounting frame allows the frame to be adapted for use with almost any size or configuration of light carrier or surgical instrument. The device is versatile, efficient and cost effective. A vast inventory of custom surgical instruments, which are capable of accommodating only a very limited number of light carriers, do not have to be purchased and maintained. An improved light projecting capability may be provided for almost any existing surgical instrument using the mounting frame of this invention. The clip version may also be used with various types of surgical tools but is especially effective for use with retractors. The dimensions, resiliency and arrangement of the clip portion and individual clips may also be varied within the scope of this invention.

The mounting frame of this invention may be utilized to install a needed light carrier on a particular surgical instrument quickly and conveniently. Using the mounting frame to attach a light carrier onto the surgical instrument is a very quick, simple and convenient procedure. This saves medical personnel considerable time in preparing for surgery. The efficiency and effectiveness of the medical procedure are therefore also likely to be improved in most cases. Accordingly, the present invention relates to a mounting frame for releasably attaching a light carrier to an underlying surgical instrument. The mounting frame enables various shapes and sizes of light carriers to be quickly, conveniently and effectively secured to an underlying instrument. The light carrier is then held in place during a surgical or medical procedure to provide for improved illumination of the procedure.

There is shown in FIGS. 11-14 light carrier C5, which includes a retaining clip portion comprising a pair of retaining clip elements 226 and 228, which are molded or otherwise formed unitarily with light carrier C5 such that the light carrier can be quickly and conveniently attached to a retractor or other surgical instrument. Light carrier C5 is molded in a single piece and is composed of a light conducting material. Preferably, this comprises a polycarbonate or alternative plastic material that is capable of transmitting and projecting light received from a fiberoptic illuminator or alternative light source. A particularly preferred material is 2458 Makrolon® Clear, although alternative materials may be employed for the light conductor within the scope of this invention.

Figure 11:
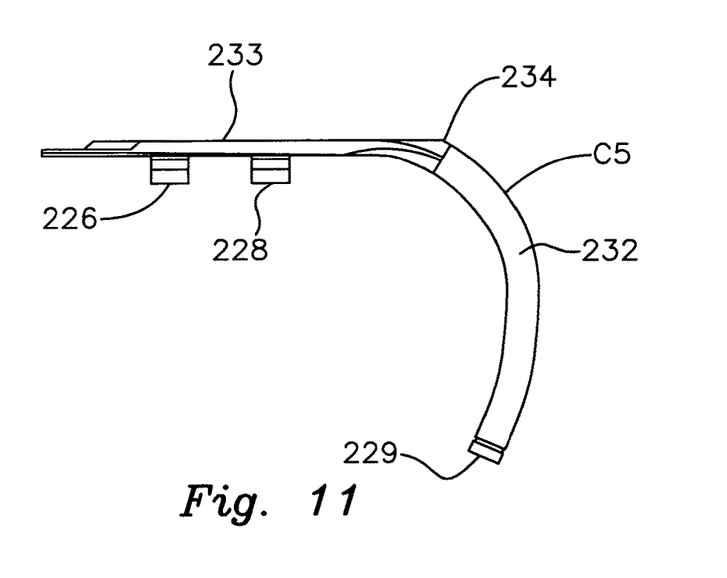
FIG. 11 is an elevational side view of a one-piece light carrier with unitary mounting clips in accordance with this invention.

Light carrier C5 specifically includes an inlet section 229, FIG. 11, that is designed to be operatively and communicably interengaged with a standard light-conductive fiberoptic cable or other light source. An elongate intermediate rod section 230 is unitarily and communicably interconnected to inlet section 229. Rod section 230 has a circular cross sectional shape, shown in FIG. 13, and features a longitudinally curved neck 232.

Figure 12:
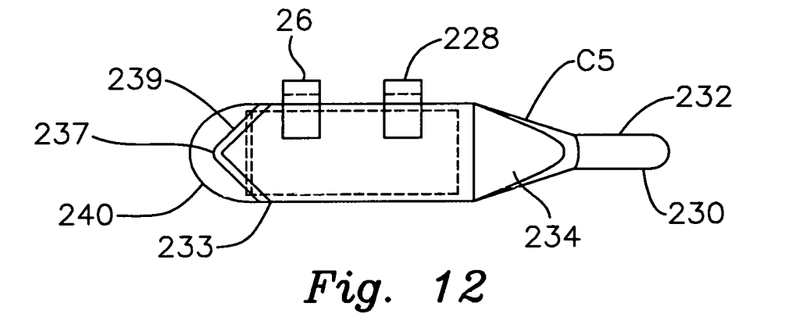
FIG. 12 is a top plan view of the light carrier of FIG. 11.
Figure 13:
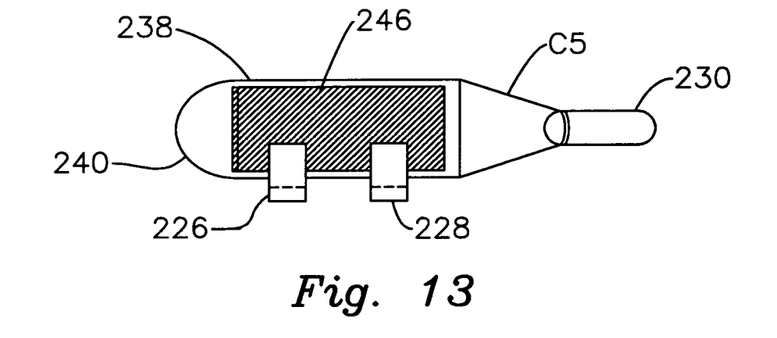
FIG. 13 is a bottom plan view of the light carrier of FIG. 11.

As shown in FIGS. 11-14, the upper end of light carrier C5 includes an elongate blade section 233, which is again composed of Makrolon® or other light-conducting material. Blade 233 has substantially flat upper and lower surfaces. The main body 235 of blade 233 extends for most of the length of the blade and terminates at a relatively pointed apex 237. The leading end of main body 235 includes a "V" shaped configuration having a rearwardly angled or beveled surface 239, FIGS. 12, 14. A relatively thin and flat tip 240 having a convex leading edge extends forwardly of main body portion 235. As best shown in FIGS. 12 and 13, the bottom surface of blade 233 includes a matte portion 246 that is etched, matted or otherwise constructed to disperse light therefrom in a broadly radiating pattern, as will be described more fully below. Resilient retaining clips 226 and 228 are unitarily connected to one longitudinal edge of blade 233 and include a cross sectional shape as shown in by representative clip 226 in FIG. 15. Each clip extends downwardly from the blade and beneath the lower surface such that the clips extend partially across the matte portion 246.

Figure 14:
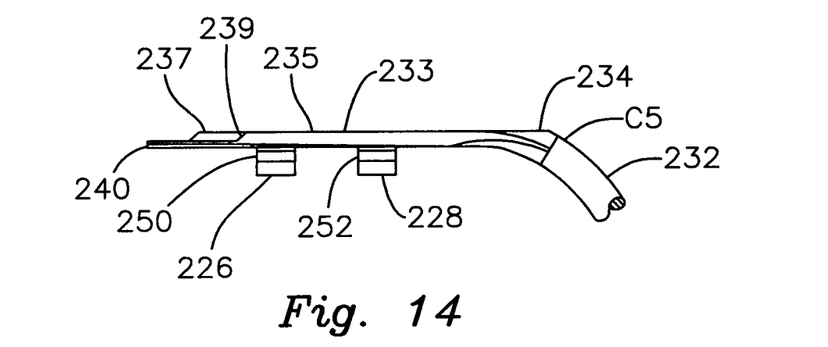
FIG. 14 is a fragmentary, side elevational view depicting the neck, transition and blade sections of the light carrier of FIG. 11.
Figure 15:
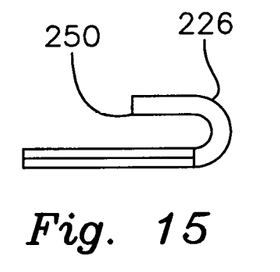
FIG. 15 is an end view of a representative clip used in the light carrier of FIGS. 11-14.

Blade section 233 is unitarily and communicably interconnected to rod section 230 by a transition section 234 of carrier C5. More particularly, transition section 234 again includes the light-conducting material as described above. Transition section 234 features a configuration that tapers in two planes. The transition section specifically narrows vertically, as best shown in FIGS. 11 and 14, from the upper end of rod 230 and neck 232 to the flat upper and lower surfaces at the right hand end of blade section 233. As a result, main body portion 235 of blade section 233 has a thickness that is less than the diameter of rod section 232. Transition section 234 also narrows laterally, as best shown in FIGS. 12 and 13, from blade section 233 to rod section 230. As a result, the transverse width between the two longitudinal sides of blade 233 is greater than the diameter of rod section 230.

The dual tapered configuration of transition section 234 is extremely important to the effective operation of blade 233. Specifically, light is essentially transmitted as a beam through rod section 230 and specifically through neck 232. The transition section 234 gradually transforms the transmitted light from a beam into a relatively broad and essentially planar light pattern that is transmitted through the wide, yet thin material comprising blade section 230. This pattern of light is then effectively dispersed and radiated from the matte portion 246. Light transmitted by blade element 233 is also projected from the pointed leading end or apex 237 of main body 235 and the convex tip 240 of blade 233. Light is thereby projected in a variety of ways by the blade of illuminator C5.

In operation, light carrier C5 is mounted to a retractor or other surgical instrument by expanding resilient clips 226 and 228 and inserting the retractor blade or other instrument part into slots 250 and 252 of clips 226 and 228, respectively. This attaches the light carrier to the retractor blade or other surgical instrument. Light carrier inlet 229 is then interengaged with a fiberoptic cable or other source of light. This delivers light through the inlet section to rod section 230. The light-conducting material of the light carrier transmits the light through neck 232 to transition section 234. The light is then essentially converted from a beam to a relatively flat and wide plane of light that is transmitted longitudinally through blade 233. The transmitted light is then dispersed through matte portion 246 and thereby projected or radiated relatively broadly so that it may effectively illuminate a surgical site Blade 233 also transmits light to and projects light from the beveled surfaces 239 and apex 237 of main body 235. This directs a relatively focused beam of light toward an intended body part or other surgical target which requires focused illumination. Light is also transmitted by the blade to convex leading tip 240, which directs a broader diverging light pattern toward an intended target. Light carrier C5 thereby allows various patterns and intensities of light to be accessed and utilized as required during surgery or other medical procedures. The light carrier provides for greatly improved versatility and improved lighting which is especially useful in surgical applications. As with the previously described versions of this invention, carrier C5 preferably includes retaining clips 225, 228 that allow the light carrier to be quickly and conveniently attached to a surgical retractor or other medical instrument used during a surgical procedure.

It should be understood that in the version shown in FIGS. 11-15, light is transmitted through and projected by all parts of the one-piece blade section. The periphery of blade section 233 also effectively serves as an upper frame portion for supporting both the above described light projecting portions of the blade and the integral or unitary clips 226 and 228. Indeed, in various alternative versions of this invention, the upper frame portion and indeed the clip portions and clip elements themselves may comprise light-conductive material analogous to that comprising the light-projecting portions of the one-piece light carrier.

The use of the transition section as previously described achieves a broader radiating illumination that is effective for illuminating surgery. The transition section and uniquely configured blade section also provide for a versatile selection of light-projecting patterns (i.e. focused beams, diverging light outputs and broad radiating light patterns). In addition, that transition section greatly improves lighting efficiency by reducing inefficient light losses. Specifically, the transition section effectively channels and directs the light beam directed through the rod section into the blade section where the light is transformed into a flatter and wider pattern, Without the use of the disclosed transition section, much if not most of the light transmitted through the rod section would be likely prematurely discharged from the blade at an angle and still in the form of a beam, and would therefore not be nearly as effective in lighting a surgical site with a broad radiating light pattern as is provided through the matte surface employed in the present invention.

Figure 16:
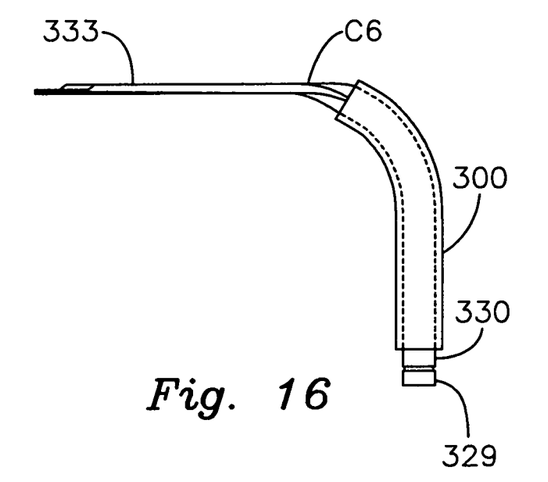
FIG. 16 is a side elevational view of an alternative light carrier employing a molded overlay that reduces light dispersion through the neck section.
Figure 17:
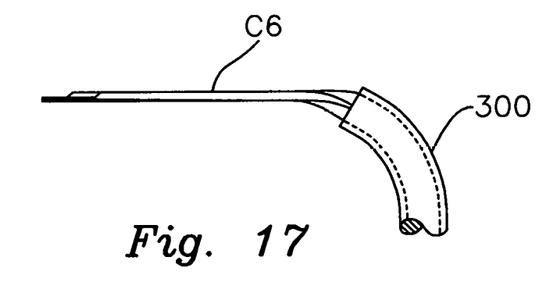
FIG. 17 is a fragmentary, elevational side view of the light carrier of FIG. 16 particularly depicting the upper end of the neck overmold as well as the transition and blade sections.
Figure 18:
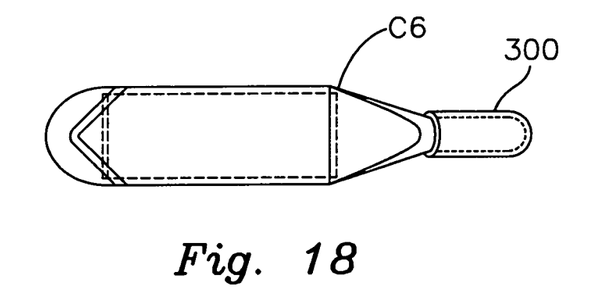
FIG. 18 is a top plan view of the light carrier and overmold shown in FIGS. 16 and 17.

In order to reduce inefficient and potentially distracting light discharge through the rod section and, more particularly, through the neck of the carrier, the neck may be provided with an overmold 300 as shown in FIGS. 16-18. Therein, light carrier C6 again includes an inlet section 329 and intermediate rod section 330 and a blade section 333, which are formed of a single piece of light-conductive material and function in a manner analogous to that previously described. In this version, a neck overlay or overmold 300 is wrapped about at least the neck of rod 330. Overmold 300 may include a thickened piece of plastic of the type comprising the light carrier. The rod and overmold may be molded together and comprise a single unitary piece of plastic. In some versions, opaque coloring may be applied to the rod section to reduce light discharge from the rod section. In still other embodiments, a relatively opaque plastic tube or sleeve may be fitted over the rod section. In either event, this feature is utilized to restrict the amount of light that is dispersed through and projected laterally from the rod section and curved neck of light carrier C6. This feature improves the efficiency of the system by eliminating premature light dissipation and enabling a greater portion of the transmitted light to be used for surgical illumination. It also avoids potentially disruptive distraction of the surgeon and medical staff which can otherwise be caused by excessive and straying light being projected outwardly from the rod section and curved neck of the carrier.

Although specific features of the invention are shown in some of the drawings and not others, this is for convenience only, as each feature may be combined with any and all of the other features in accordance with this invention.

What is claimed is:

1. An illuminating assembly attachable to an elongate retractor blade of a surgical retractor for use in a medical or surgical procedure, said illuminating assembly comprising:
    an elongate light carrier that is operably connectable to a light source for transmitting light through said light carrier, which light carrier includes a light-projecting exterior surface;
    an upper frame portion having a receptacle that has a substantially flat base extending fully between and through open and unobstructed leading and trailing ends of said receptacle, said receptacle being further defined by a pair of light carrier retaining longitudinal side walls of said upper frame portion, which longitudinal side walls extend upwardly from and are unitarily connected to said base for holding the light carrier within said receptacle of said upper frame portion such that the light projecting exterior surface of the light carrier is exposed between said light carrier retaining longitudinal side walls; and
    a retaining clip portion unitarily attached to said upper frame portion as a single piece, said retaining clip portion having a passageway with open and unobstructed leading and trailing ends, which passageway extends substantially parallel to said receptacle of said frame and configured for receiving the surgical retractor blade and releasably holding said retractor blade such that said light carrier is superposed conformably above and extends generally parallel to the retractor blade with the light projecting portion exterior surface of the light carrier exposed by said upper frame portion, whereby light transmitted through the light carrier is projected by the light projecting portion exterior surface to illuminate a surgical or medical procedure involving the surgical instrument retractor blade.

2. The device of claim 1 in which said retaining clip portion includes a least one bendable retaining clip attached to said upper frame portion.

3. The device of claim 1 in which said retaining clip portion includes a wall that depends from said receptacle and a curved backing element attached to a lower end of said wall and spaced apart from said base of said receptacle to define a channel for receiving the surgical instrument retractor, said light carrier and said retractor blade being extendable through said open and unobstructed leading and trailing ends of said receptacle and said passageway respectively.

4. The device of claim 3 in which said curved backing element is for bearing resiliently against the retractor blade such that the retractor blade is retained between said curved backing element and said base of said receptacle.

5. An illuminated surgical retractor assembly for use in medical and surgical procedures, said retractor assembly comprising:
    a surgical retractor adapted for use in a medical or surgical procedure, said retractor including an elongate retractor blade;
    an elongate light carrier that is operably connectable to a light source for transmitting light through said light carrier, which light carrier includes a light-projecting exterior surface; and
    a mounting device for releasably attaching said light carrier to said retractor blade said mounting device including an upper frame having a receptacle that has a substantially flat base extending fully between and through open and unobstructed leading and trailing ends of said receptacle, said receptacle being further defined by a pair of light carrier retaining longitudinal side walls of said upper frame portion, which longitudinal side walls extend upwardly from and are unitarily connected to said base for holding the light carrier within said receptacle of said upper frame portion such that the lights projecting exterior surface of the light carrier is exposed between said light carrier retaining longitudinal side walls; and a retaining clip portion unitarily attached to said upper frame portion as a single piece, said retaining clip portion having a passageway with open and unobstructed leading and trailing ends, which passageway extends substantially parallel to said receptacle of said frame and configured for receiving the surgical retractor blade and releasably holding said retractor blade such that said light carrier is superposed above and extends generally parallel to the retractor blade with the light projecting exterior surface of the light carrier exposed by said upper frame portion, whereby light transmitted through the light carrier is projected by the light projecting exterior surface to illuminate a surgical or medical procedure involving said retractor blade.

6. The device of claim 5 in which said retaining clip portion includes at least one bendable retaining clip attached to said, upper frame portion.

7. The device of claim 5 in which said retaining clip portion includes a wall that depends from said receptacle and a curved backing element attached to a lower end of said wall and spaced apart from said base of said receptacle to define a channel for receiving the surgical retractor, said light carrier and said retractor blade being extendable through said open and unobstructed leading and trailing ends of said receptacle and said passageway respectively.

8. The device of claim 7 in which said curved backing element is for bearing resiliently against said retractor blade such that the said retractor blade is retained between said curved backing element and said base of said receptacle.

9. The device of claim 6 in which said retaining clip portion is resiliently expandable and unitarily connected to said upper frame portion, said clip portion being selectively expanded to engage and attach to the surgical retractor blade.

* * * * *

UNITED STATES PATENT AND TRADEMARK OFFICE
CERTIFICATE OF CORRECTION

PATENT NO. : 10,463,444 B2
APPLICATION NO. : 15/172764
DATED : November 5, 2019
INVENTOR(S) : James M. Davis and Kim A. Marsh Page 1 of 1

It is certified that error appears in the above-identified patent and that said Letters Patent is hereby corrected as shown below:

On the Title Page

Item (60) under the heading "Related U.S. Application Data", add the following:
--Continuation-in-part of application No. 14/880,632, filed on October 12, 2015, now Pat. No. 10,064,613, which claims the benefit of Provisional application No. 62/062,329, filed October 10, 2014--.

Signed and Sealed this
Eleventh Day of August, 2020

Andrei Iancu
*Director of the United States Patent and Trademark Office*